United States Patent [19]

Secunda

[11] 4,424,814
[45] Jan. 10, 1984

[54] PERFUSION RATIO DETECTOR

[76] Inventor: Jeffrey Secunda, 44 Harold St., Sharon, Mass. 02067

[21] Appl. No.: 249,071

[22] Filed: Mar. 30, 1981

[51] Int. Cl.$^3$ ............................................. A61B 10/00
[52] U.S. Cl. ..................................................... 128/663
[58] Field of Search ................ 128/663, 666, 687–694, 128/713

[56] References Cited

U.S. PATENT DOCUMENTS

| | | | |
|---|---|---|---|
| 3,796,213 | 3/1974 | Stephens | 128/666 |
| 3,980,075 | 9/1976 | Heule | 128/666 |
| 4,094,308 | 6/1978 | Cormier | 128/715 |
| 4,109,643 | 8/1978 | Bond et al. | 128/666 |
| 4,147,059 | 4/1979 | Fathauer | 128/663 |
| 4,167,331 | 9/1979 | Nielsen | 128/633 |

Primary Examiner—Kyle L. Howell
Assistant Examiner—Francis J. Jaworski
Attorney, Agent, or Firm—Wolf, Greenfield & Sacks

[57] ABSTRACT

The detector provides an effective means of non-invasively monitoring the perfusion of blood by external cardiac massage during a cardiac arrest. A Doppler probe is adhesively placed on the patient's skin, preferably to sense the carotid pulse which has been found as the most significant indicator of sufficient cerebral perfusion. The electronic part of the detector measures both the period of blood flow ($T_f$), and the period of the external cardiac massage (ECM) cycle ($T_{ecm}$). The electronic components comprise a flow detector such as a Doppler sensor and Schmidtt trigger, a rate converter such as a frequency to voltage converter feeding a voltage controlled oscillator, and a counter and display. The preferred display is a series of ten light indicators for demarcating perfusion ratio in 10% increments.

10 Claims, 6 Drawing Figures

TIMING DIAGRAM

PERFUSION RATIO DETECTOR

BACKGROUND OF THE INVENTION

The present invention relates to a detector for providing an effective means for non-invasively monitoring the perfusion ratio which is an indication of the efficiency of the perfusion of blood by external cardiac massage during a cardiac arrest. The device described herein is also particularly adapted to provide an immediate feedback to the person providing cardiopulmonary resuscitation (CPR) as to the efficacy of the external cardiac massage (ECM) as indicated by the ratio of the perfusion period to the period of the (ECM).

There have been many endeavors to improve the techniques associated with the management of cardiac arrest. The development of electro-cardiograph (ECG) equipment enables doctors to observe, through non-invasive means, the electrical activity of the heart. This provides valuable information for the diagnosis and treatment of various cardiac problems. Lightweight, battery powered (ECG) recorders have been developed to provide field deployment capabilities. The development of the cardiac defibrillator is also important especially in the treatment of certain electrical problems of the heart, and has also been designed to travel with emergency teams into the field. The potential danger associated with the defibrillator, however, has limited use basically only to those people under the direct supervision of a physician. The development of the modern technique of cardio-pulmonary resuscitation (CPR) has proved to be an effective means of managing the cardiac arrest patient in lieu of more sophisticated techniques, and equipment associated with a hospital trauma center or operating room. (CPR) makes use of external cardiac massage (ECM) to perfuse the patient's blood by compressing the heart between the sternum and the spine. The person administering the (ECM) is required to push quite hard and also sufficiently long on the patient's chest to move the bllod throughout the patient's circulatory system. Research by many investigators, outlined hereinafter, has indicated that the ratio of the period of blood perfusion time to the period of the (ECM) is a critical factor in providing an adequate blood supply to the patient's brain. However, the efficacy of (ECM) is difficult to monitor non-invasively. One common indication of efficacy is the dilation of the pupils, indicating inadequate perfusion to the brain and probable brain damage. Clearly this is not an effective indicator. Thus, the purpose of the device of the present invention is to provide an immediate feedback as to the efficacy of the (ECM) as indicated by the ratio of the perfusion period to the period of the (ECM).

PRIOR ART

Grunau, CFV.: Doppler Ultrasound Monitoring of Systemic Blood Flow During CPR. JACEP 7:5, 1978, discloses that the amplified audio output of a Doppler flow detector may be used for the assessment of external cardiac massage (ECM). Grunau employs a Doppler ultrasound instrument and ultrasound transducer. The transducer crystals are mounted within the flat probe at a 45° angle, with respect to the plane that they are in contact with. The output of the Doppler and the (ECG) output of cardioscope are recorded on a two-channel thermal chart recorder, located in an area which is remote from the site where the CPR is performed. This technique was used exclusively in the emergency room of a hospital. The Grunau report also mentioned the attachment of the Doppler probe over the radial artery of an incoming cardiac arrest patient. This technique was, as mentioned previously, primarily only for use in an emergency room and was not adapted to portable use at all.

Lichti, EL, et al: Cardiac Massage Efficacy Monitored by Doppler Ultrasound Flowmeter. Mo Med 68: May, 1971, reported that while the healthy heart is capable of perfusion for 70% of the cardiac cycle, it was not unusual to find that blood was only perfuused for 20% of the ECM cycle during CPR. A husky fireman can induce instantaneous pressure of over 300 mmHg without perfusing much blood unless he maintains the compression for at least half the ECM cycle. It is a difficult physical task to maintain ECM pressure against the spring effect exhibited by the sternum and ribs.

Roberts, BG: Machine CPR vs. Manual CPR in Moving Vehicles. Proceedings: American Asssociation for Automotive Medicine, and others have advocated the use of a mechanical resuscitator to improve perfusion time. While this device can be adjusted to deliver 70% compression at a specific force and rate, it has not been widely accepted due to the possibility of fracturing ribs if the device is set up incorrectly or slips out of position. Also, the device is expensive and requires large quantities of oxygen to drive the unit, thus also hindering the acceptance of this mechanical resuscitator.

Taylor, GJ, et al: Importance of Prolonged Compression During Cardiopulmonary Resuscitation in Man. NEJM 296:26, 1977. Vaagenes, P: On the Technique of External Cardiac Compression. Crit Care Med 6:3, 1978, along with others, have pointed toward sustanining the compression phase of ECM as a method of increasing the mean arterial pressure (MAP) and thus the perfusion of blood to the brain. The non-invasive measurement of mean arterial pressure, on a beat-to-beat basis, however, has yet to be demonstrated clinically.

THE INVENTION

One of the objects of the present invention is thus to provide an effective means of measuring perfusion time in the environment of field administered CPR, a non-invasive technique is of utmost importance. Furthermore, in such an environment it is important that there be provided a feedback display which is instantaneously usable by the CPR technician or team. In this regard, the recorder output that has previously been present from the Doppler generator is not an adequate feedback device because of all of the interpretation required to relate the shape of the blood velocity waveform to the ratio of perfusion time to ECM cycle time.

Accordingly, it is the object of this invention to provide, not only a non-invasive technique for measuring efficacy, but also a detector which instantaneously records the perfusion ratio which is a ratio of perfusion time to ECM cycle time.

In an arrangement such as taught by Grunau, infra, it has been found that the audio output of the Doppler is extremely difficult to use during CPR due to at least two major factors. The first factor is the variability of the Doppler sound. The Doppler detects the velocity of the blood flowing through a vessel. Therefore, if the cross-sectional area of the vessel is reduced by increased pressure of the Doppler probe, the velocity of the blood increases without a significant change in systemic pressure. Any variation in the probe attachment pressure will thus create confusing changes in the Doppler audio output.

The second problem experienced in the user of the Doppler output stemmed from the ambient noise conditions at the scene of most cardiac arrests, whether at a private home or elsewhere. Noise from the electronic siren, directly over the heads of the paramedics in a travelling ambulance can easily exceed 100 db. Also, the paramedics usually have to maintain radio contact with the attending physician at the hospital and communicate between the hospital concerning the patient's vital signs and medication. The audio environment is too cluttered to allow effective use of the Doppler.

The problems referred to herein are overcome by selection of the proper site for application of the Doppler probe and by special filtering described hereinafter used in connection with the Doppler detection. Grunau used the radial artery pulse as the prime site for the attachment of the Doppler probe. This site, however, has been found to not be successful because of the weak and noisy signals that have been recorded. In this technique the probe well is filled with acoustic coupling medium and fixed on the wrist by either adhesive tape or an elasticized Velcro strip. In this arrangement the crystal itself of the Doppler probe is not directly in contact with the skin. Both techniques of fixation were hampered by the difficulty in regulating the pressure of the probe over the radial artery. As stated earlier, too much pressure will increase the velocity of the blood, or ultimately occlude the artery; too little pressure will allow the coupling means to leak out and will allow probe movement on the wrist to generate noise.

The pulse in the brachial artery provides a slightly stronger signal than the radial artery pulse. However, as described hereinafter, the most significant pulse point has been found to be the carotid pulse. The selection of the proper site for attachment of the Doppler probe came about after investigating the hemodynamics of the body during cardiac arrest. The body attempts to survive a cardiac arrest with several maneuvers. As the cardiac output decreases during an arrest, sympathetic nervous stimulation increases the tendency for venous return by increasing venous tonus. This decreases peripheral venous resistance, which raises the systemic filling pressure of the heart and thus increases the pumping efficacy of the heart. Fluid retention by the renal system tends to increase cardiac output by increasing the fluid volume of the circulatory system and also by reducing venous resistance. Ultimately, the purpose of maintaining the cardiac output is to provide adequate perfusion of oxygenated blood to the brain. As a result, the peripheral arterial resistance is increased in order to direct the main effort of the heart towards perfusing the brain. This analysis of cardiac arrest hemodynamics, points toward the carotid pulse as the most significant indicator of sufficient cerebral perfusion. Thus, in accordance with the present invention this is the preferred location for the Doppler probe. The Doppler probe is affixed over the carotid pulse with an adhesive foam patch. The adhesive patch proves to be an effective means of maintaining probe stability and preventing the acoustic coupling medium from leaking out of the probe well. The skin is prepared by degreasing with an alcohol wipe.

In addition to the proper placement of the Doppler probe for detection, in accordance with the invention, there is also developed an effective means for the paramedics or others to judge the efficacy of their ECM. As mentioned previously in accordance with the invention this is a non-invasive technique that has associated therewith immediate feedback for instantaneously indicating to the CPR technician or team what type of efficiency is being applied in applying the CPR technique.

In accordance with the invention the detector uses the Doppler technique to measure both the period of blood flow, and the period of the ECM cycle. By measuring the flow period, instead of the velocity, the stability of the probe attachment site becomes less critical. In that only the beginning and end of the flow waveform are of interest, greater filtration of noise may be tolerated without significant loss of data. In accordance with the invention the detector comprises a flow detector which includes the Doppler detector and a trigger device such as a Schmidtt trigger. The detector also includes a rate converter which may comprise a frequency to voltage converter and voltage controlled oscillator, along with a counter and display means. The Schmidtt trigger is used to detect the beginning and end of the flow period. Heavy filtering is employed to reduce noise and allow the Schmidtt trigger to be set extremely low. The rate converter provides a 1:10 conversion of the rate of ECM, as detected by the Schmidtt trigger. Thus, the measured value of the flow period is proportional to the rate of ECM. The output of the decimal counter, therefore, is a number representative of the ratio of the detected flow period to the rate of ECM. This output is then used to drive indicators which are continuously updated to indicate perfusion ratio. The preferred display means includes a series of ten light indicators such as light emitting diodes for demarcating perfusion ratio in 10% increments.

BRIEF DESCRIPTION OF THE DRAWINGS

Numerous other objects, features and advantages of the invention should now become apparent upon a reading of the detailed description taken in conjunction with the accompanying drawings, in which.

DETAILED DESCRIPTION

Figure 1:
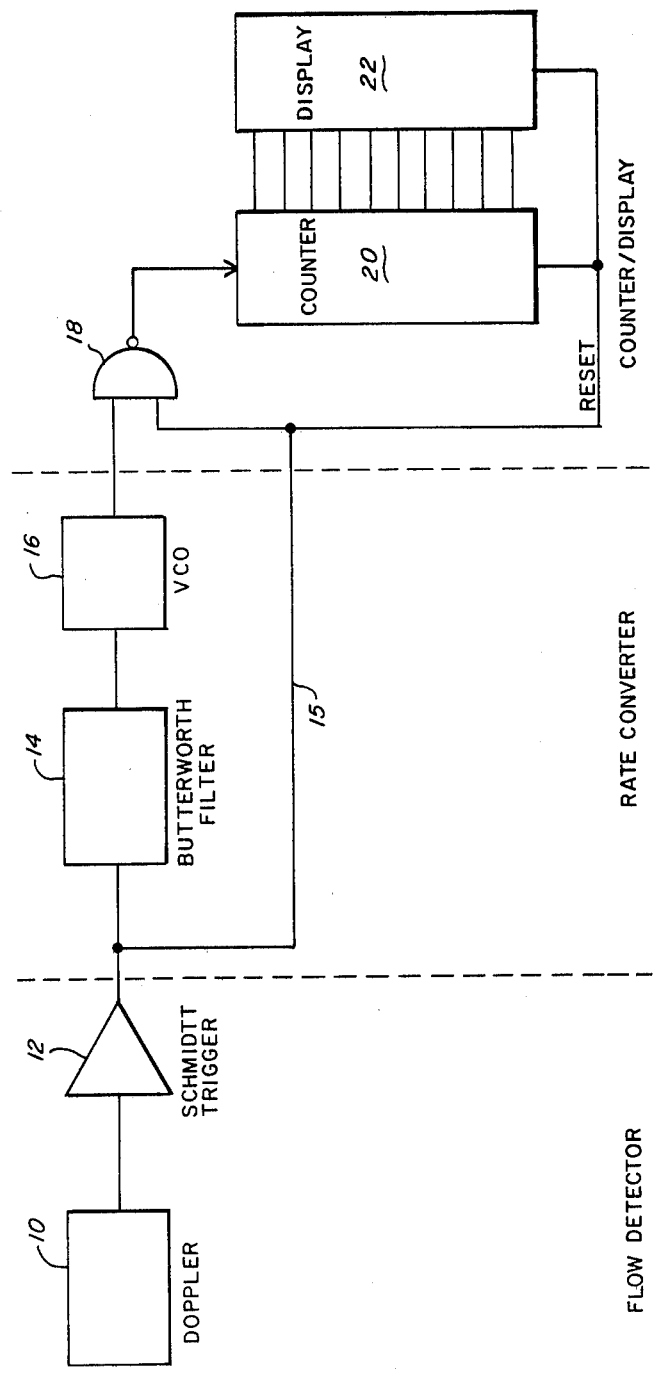
FIG. 1 is a block diagram showing the basic building blocks in the preferred embodiment of the present invention.
Figure 3:
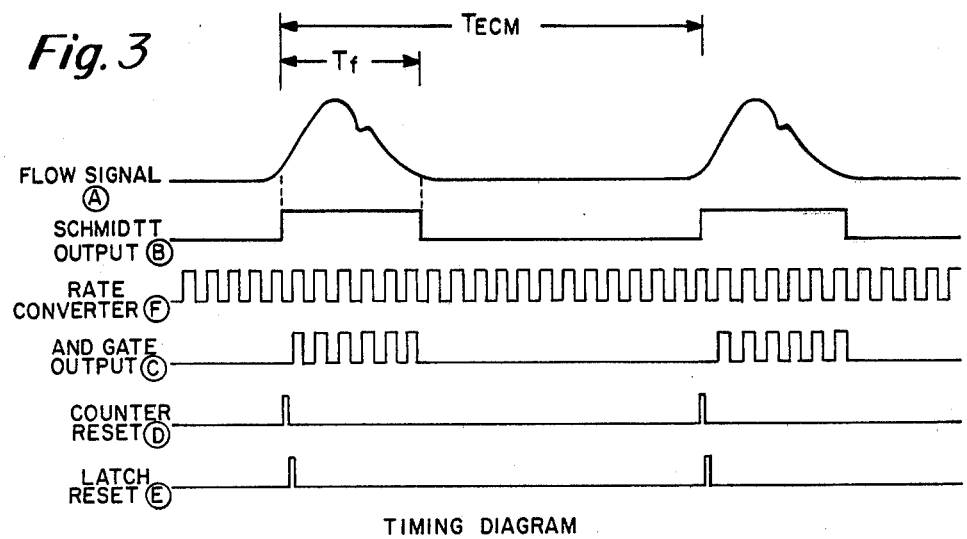
FIG. 3 is a timing diagram associated with the circuit of FIG. 2.

FIG. 1 is a block diagram showing the major components of the device or detector of this invention. The three basic components include a flow detector, a rate converter, and a counter/display. The flow detector includes a Doppler detector 10 which includes a Doppler probe (crystal) and an ultrasonic Doppler flow detector such as the Parks 822 Doppler flow detector. Such a detector conventionally provides an analog recorder output which converts the frequency difference of the Doppler shifted signal to a voltage. Thus, the greater the velocity of the flow, the larger the frequency shift, and the larger the resultant amplitude of the recorder output. The Parks 822 also provides low pass filtering at the output. Substantial filtering ($f_h = 4.5$ Hz) is employed to reduce noise and to allow the Schmidtt trigger to be set at a very low threshhold level. It is because the perfusion ratio is not dependent on the velocity waveform, but rather on the event of blood flow, that a significant degree of filtering by the Doppler flow detector is possible to provide a noise and motion artifact free signal to the input of the Schmidtt trigger 12. This Schmidtt trigger 12 detects the beginning and end of the flow event. Reference is also made to FIG. 3 wherein this signal is shown at FIG. 3A. The Schmidtt trigger output is shown at FIG. 3B.

The rate converter shown in FIG. 1 includes a Butterworth filter 14 and a voltage controlled oscillator 16. The output from the Schmidtt trigger 12 also couples by way of line 15 as both a reset for the counter/display and one input to the gate 18. Thus, the output of the Schmidtt trigger is used to reset the counter/display at the start of each flow event, enables the gate 18 for the duration of each flow event, and provides the input signal to the rate converter.

When the Schmidtt trigger goes high at the start of a flow pulse such as the ones depicted in FIG. 3A, the NAND gate 18 is enabled and the output from the rate converter is used to measure the period of the flow pulse. The rate converter provides a 1:10 conversion of the rate of ECM, as detected by the Schmidtt trigger. Thus, the measured value of the flow period is proportional to the rate of ECM. The output of the gate 18 it is noted, couples to the counter 20 and the outputs from the counter couple to the display 22. The output of the decimal counter is an expression of the ratio of the detected flow period to the rate of ECM. The display 22, as discussed hereinafter, is a series of light emitting diodes that provides demarcation of the perfusion ratio in 10% increments.

Considering a rate of 60 compressions per minute (one compression per second), the rate converter has an output of 10 Hz. If the flow period is 0.5 seconds, then the decimal counter receives 5 clock pulses from the rate converter during the 0.5 second period when the Schmidtt trigger has enabled the NAND gate 18. The count of 5 on the display is interpreted as a flow ratio of 50%. In this regard, note FIG. 5 and the indicators 24 shown in 10% increments. As the flow period increases, at the same ECM rate, the counter displays a larger number indicating a larger flow ratio. On the other hand as the ECM rate changes such as the rate increasing, to say, 90 compressions per minute (1.5 compressions per second), the rate converter output increases proportionally to 15 Hz. A flow period of 1.5 seconds now yields 7.5 clock pulses to the decimal counter indicating a flow ratio of 75%. This would be indicated in the embodiment of FIG. 5 by either the indicator for 70% or 80% being illuminated, or in an alternate arrangement all indicators could be illuminated therebelow. Also, other versions could employ 5% demarcations rather than 10%. Preferably, as the counter is clocked by the rate converter, successive indicators are latched on, essentially providing a bar graph type display. At the start of each flow pulse, the preceding count is reset and thus the display is essentially updated for each event.

Figure 5:
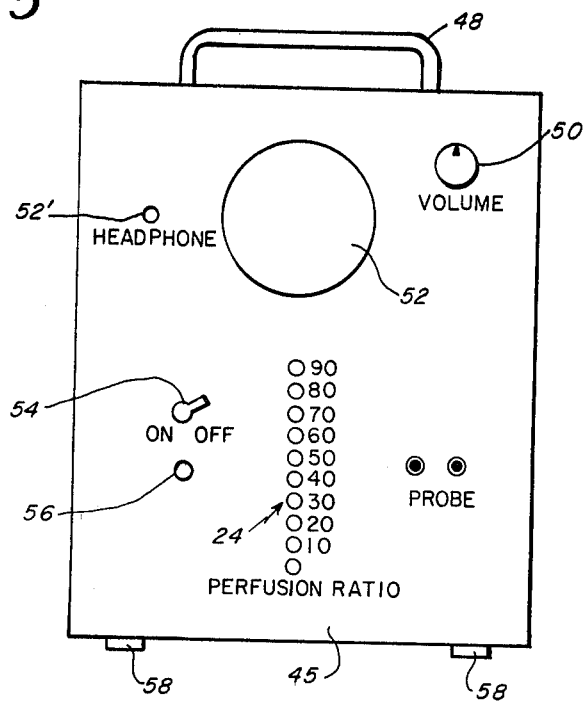
FIG. 5 shows the apparatus of the present invention as contained in a housing including the LED display for instantaneously displaying the perfusion ratio.

This noninvasive measurement technique, along with the display technique provides immediate feedback to the rescuer as to the ultimate effectiveness of the ECM as expressed as the ratio or perfusion to ECM cycle time. The device may be easily installed inside an existing Doppler unit such as the Parks 822, with the LED display mounted on the control panel. FIG. 5 shows such an arrangement that may either be a modification of the Parks equipment or a different design.

Figure 2:
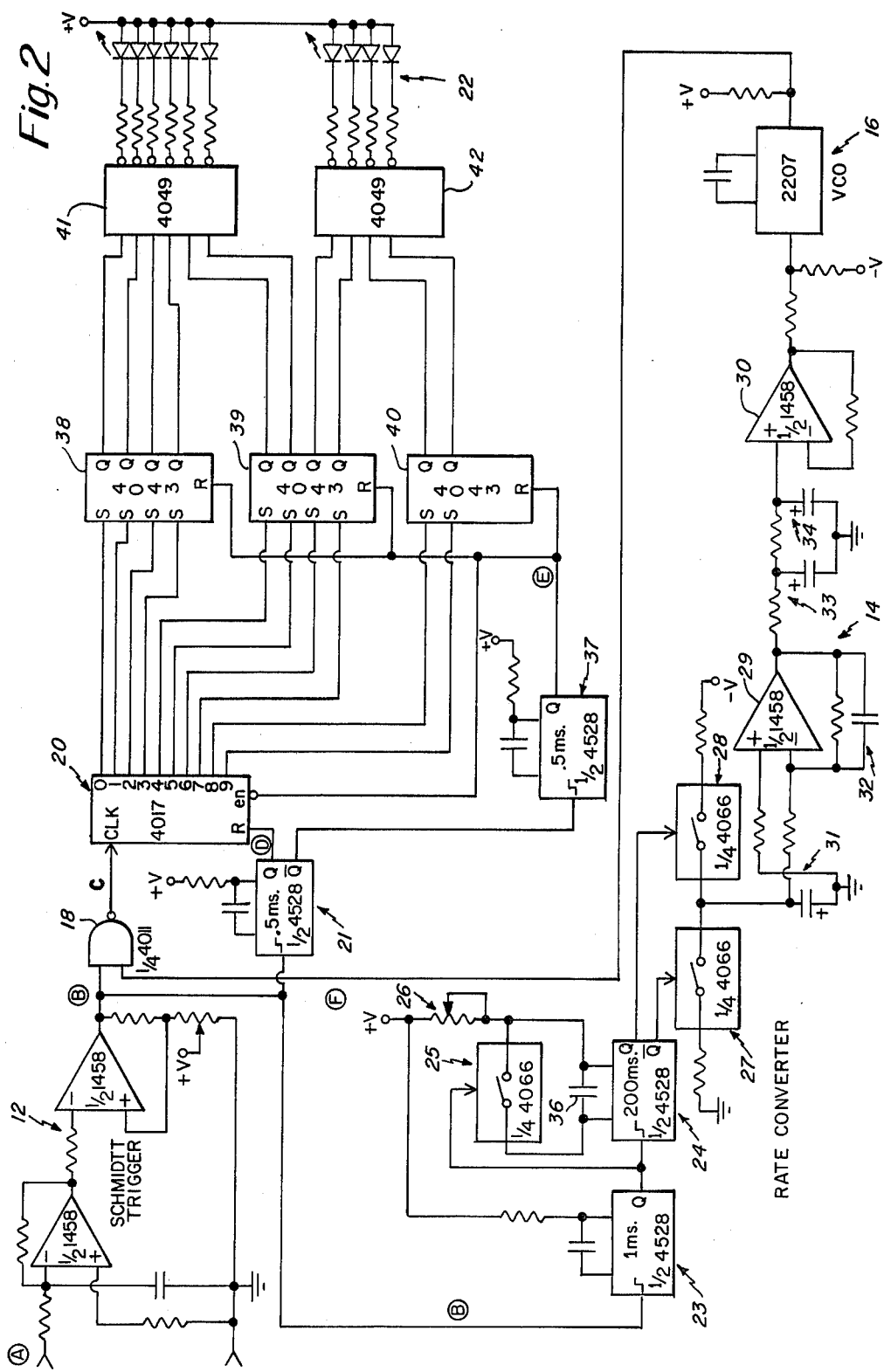
FIG. 2 is a circuit diagram showing the complete details of the block diagram of FIG. 1.

FIG. 2 is a complete schematic diagram of the block diagram of FIG. 1. In FIG. 2 each of the components are of conventional design and each is indicated by its corresponding conventional indication. For example, the counter 20 is a type 4017. This counter has a plurality of outputs, a clock input, a reset input and an enable input.

The rate converter receives it input from the output of the Schmidtt trigger 12 indicated at point B. The signal at this point is also indicated in the timing diagram of FIG. 3. This signal fires the 1 millisecond one-shot 23, activating the analogue switch 25 which discharges the timing capacitor 36 and triggers the 200 millisecond one-shot 24. At the start of the 200 millisecond timing cycle, the analogue switch 27 applies the voltage $-V$ to the input of the 4 pole Butterworth filter 14. If the 1 millisecond one-shot 23 fires again before the end of the 200 millisecond timing cycle, the analogue switch 25 activates, shorting the timing capacitor 36 and retriggering the 200 millisecond timing cycle. The Butterworth filter 14 is comprised of operational amplifiers 29 and 30 along with the 4 poles (RC circuits) 31, 32, 33, and 34. Each of these poles has a time constant of 1 second. The output of the filter couples to the voltage control oscillator 16. The circuit arrangement is constructed so that 60 events per minute yield an output from the filter of 600 millivolts. The output of the filter is interfaced to a voltage controll oscillator 16 which provides a voltage to frequency conversion such that the 600 millivolts equals 10 Hz.

By way of further example, if the event frequency is 30 ppm then the output of the filter is $-0.3$ V and the output from the voltage control oscillator is 5 Hz. At an event frequency of 60 ppm the output of the filter is $-0.6$ V and the output from the voltage control oscillator is 10 Hz. For an event frequency of 120 ppm the output of this filter is $-1.2$ V and the output from the voltage control oscillator is 20 Hz.

At the beginning of each flow event the Schmidtt trigger 12 fires the one-shot 21 which resets the decimal decoded counter 20. The negation output from the device 21 provides a 0.5 second delay before firing one-shot 37. The assertion output from the one-shot 37 disables the counter 20 while resetting the output latches 38, 39, and 40. After the resetting is complete the one-shot 37 at its assertion output provides the enable signal to the counter 20. The output from the rate converter referred to as output F also shown in FIG. 3 is coupled to one input of the NAND gate 18. The other input to this gate is directly from the output of the Schmidtt trigger. Thus, the output of the rate converter is essentially counted during the duration of the output from the Schmidtt trigger which is an indication of the duration of the flow event. As the counter advances successive sections of the quad latches 38, 39, and 40 are set. The assertion outputs from these latches enable successive sections of the hex inverting output buffers 41 and 42 which turn on the light emitting diodes 24 comprising the display 22. These indicators 24 as mentioned previously, are shown on the front panel 45 of the perfusion ratio device.

At the start of each flow event the Schmidtt trigger output goes high, which enables the gate 18 as described previously. This allows the rate converter to advance the counter. The value of the flow period ($T_f$) is measured with a clock rate proportional to the rate of ECM ($R_{ecm}$). The rate is inversely proportional to period or, $$R_{ecm} = 1/T_{ecm}$$

where $T_{ecm}$ is the period of ECM. The counter contains a value of $T_f$ measured by $1/T_{ecm}$. Therefore, the output LEDs are an expression of the ratio of the flow period to the ECM period, or $$\text{Perfusion Ratio} = T_f/T_{ecm}$$

FIG. 5 shows the housing which may be a modified conventional housing such as the Parks 822 instrument. This includes a front control panel 45 in a series of indicators 24. FIG. 5 clearly indicates the demarcation of 10% values for the indicators. The electronics works so that for each flow event the indicators are counted up from the bottom until the maximum count is reached corresponding to increments of 10% of our perfusion ratio. After the flow event and prior to the next flow event then resetting occurs to then count up for the next flow event to determine perfusion ratio. In the timing diagram notice the resetting occurring just at the beginning of the flow event. The housing shown in FIG. 5 also has a handle 48, a volume control 50, an audio speaker 52, and a jack 52 for a headphone. There may also be provided on the panel an on off switch 54 and a power light 56. Preferably there is a power switch 54 and a power light 56. Preferably there are feet 58 for supporting the housing.

Figure 4A:
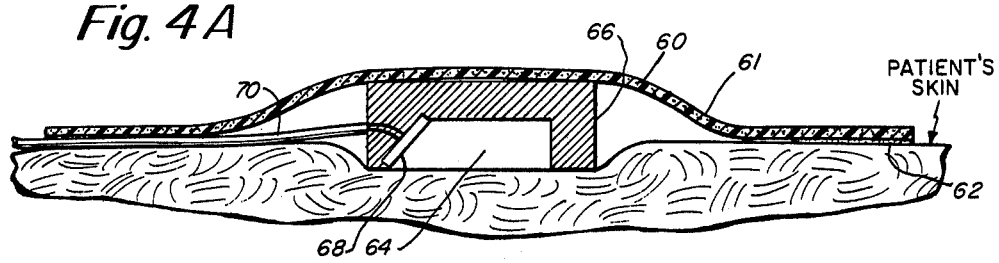
FIGS. 4A and 4B illustrate the Doppler probe and the technique of attachment.
Figure 4B:
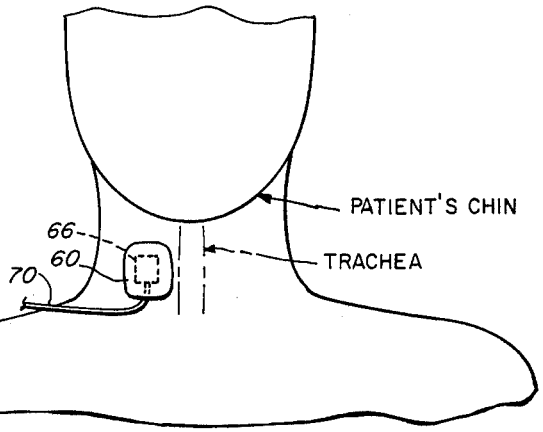

FIGS. 4A and 4B depict the manner in which the Doppler probe is secured to the patient. This probe is an ½ inch square flat Doppler probe which is held in place on the patients skin by preferably a 1 inch square patch of adhesive backed foam. In FIG. 4 note the adhesive foam material 60 which includes foam 61 and the adhesive material 62. The probe well 64 formed in the probe housing 66 contains an acoustic coupling medium which permits the ultra-sound signal penetrate the patient and detect the flow of blood. Also shown in the drawing is the detection crystal 68. A probe cable 70 connects two of the crystals 68. The adhesive patch allows for a tight seal between the patients skin and the probe preventing leakage of the coupling medium. The probe is attached to the patient over the carotid pulse for reasons discussed previously. The aggressive nature of the adhesive used on the path, makes it well suited to maintaining good probe placement under rigorous conditions encountered during a cardiac arrest. Prior to application of the adhesive foam patch the skin is preferably degreased with an alcohol wipe.

Having described one preferred embodiment of the present invention, it should now become apparent to those skilled in the art that numerous other embodiments are contemplated as falling within the scope of this invention.

What is claimed is:

1. A perfusion ratio detector comprising;
   means for detecting blood flow through the body including non-invasive ultrasonic detection means adapted for contact with the patient's skin about a pressure point of the body,
   means coupled from said detecting means for providing a pulse signal the duration of which is representative of flow period,
   rate converter means coupled from said detection means responsive to the flow period signal and including means for providing a cyclic signal of frequency greater than the rate of the flow period pulse signal,
   gate means for receiving said flow period and cyclic signals to provide a gated pulse train representative of perfusion ratio,
   means for counting said gated pulse train,
   and means coupled from said means for counting for displaying, substantially instantaneously upon occurrence of said flow period signal, a visual indication of perfusion ratio so as to immediately inform the observer as to the efficacy of perfusion flow.

2. A persusion ratio detector as set forth in claim 1 wherein said means for detecting includes Doppler detection means.

3. A perfusion ratio detector as set forth in claim 2 including a Doppler probe and means for securing the Doppler probe to the body including an adhesive foam patch.

4. A perfusion ratio detector as set forth in claim 3 wherein the Doppler probe is placed over the carotid pulse point.

5. A perfusion ratio detector as set forth in claim 1 wherein said means for providing a flow period signal includes a Schmidtt trigger type circuit for providing a pulse the width of which is representative of flow period.

6. A perfusion ratio detector as set forth in claim 1 wherein the rate converter means comprises filter means for providing an output in amplitude corresponding to input frequency, and a voltage controlled oscillator for converting the amplitude to a frequency.

7. A perfusion ratio detector as set forth in claim 6 wherein the rate converter provides a conversion ratio on the order of 1:10.

8. A perfusion ratio detector as set forth in claim 1 wherein said display means includes a series of light indicators demarcated in increments of perfusion ratio from 0–100%.

9. A perfusion ratio detector as set forth in claim 8 wherein the indicators are successively illuminated after flow event to reach the indicator of highest ratio.

10. A perfusion ratio detector as set forth in claim 9 wherein the indicators are at least ten demarcating 10% intervals of perfusion ratio.

* * * * *